US00PP23212P3

(12) United States Plant Patent
Ranney

(10) Patent No.: US PP23,212 P3
(45) Date of Patent: Nov. 27, 2012

(54) ***WEIGELA* SHRUB NAMED 'SUNSET'**

(50) Latin Name: *Weigela florida*
Varietal Denomination: Sunset

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 48 days.

(21) Appl. No.: 12/927,638

(22) Filed: Nov. 19, 2010

(65) Prior Publication Data

US 2012/0131709 P1 May 24, 2012

(51) Int. Cl.
*A01H 5/00* (2006.01)

(52) U.S. Cl. ..... Plt./226

(58) Field of Classification Search ..... Plt./226
See application file for complete search history.

*Primary Examiner* — June Hwu

(74) *Attorney, Agent, or Firm* — Michael Best & Friedrich LLP

(57) ABSTRACT

'Sunset' is a new *weigela* shrub particularly distinguished by its semi-dwarf habit, and unique variegated foliage with green centers and multicolored margins ranging from and including ivory yellow, yellow, yellow-green, green, and red depending on plant age and the time of year, is disclosed.

3 Drawing Sheets

Genus and species: *Weigela florida*.
Variety denomination: 'Sunset'.

BACKGROUND OF THE NEW PLANT

The present invention comprises a new and distinct variety of *weigela*, botanically known as *Weigela florida* and hereinafter referred to by the variety name 'Sunset'. 'Sunset' was developed and selected in Mills River, N.C. 'Sunset' is a chance seedling from an open-pollinated, *Weigela florida* designated 'Alexandra' (U.S. Plant Pat. No. 10,772). The first asexual propagation of 'Sunset' was carried out in the summer of 2004 by rooting stem cuttings in Mills River, N.C. 'Sunset' has been asexually reproduced repeatedly by softwood cuttings in North Carolina over a 6 year period.

'Sunset' roots readily from softwood cuttings from plants treated with a basal dip of 2,500 ppm indole butyric acid (potassium salt) in water. 'Sunset' has been found to retain its distinctive characteristics through successive asexual propagations via softwood cuttings.

Plant Breeder's Rights for this variety have not been applied for. 'Sunset' has not been made publicly available or sold more than one year prior to the filing date of this application.

SUMMARY OF THE INVENTION

The following are the most outstanding and distinguishing characteristics of this new variety when grown under normal horticultural practices at in Mills River, N.C.

1. A compact, semi-dwarf shrub habit; and
2. Unique variegated foliage with green centers and multicolored margins ranging from and including ivory yellow, yellow, yellow-green, green, and red depending on age of foliage and time of year.

DESCRIPTION OF THE PHOTOGRAPHS

This new *weigela* variety is illustrated by the accompanying photographs which show the plant's form, foliage and inflorescences. The colors shown are as true as can be reasonably obtained by conventional photographic procedures. The photographs were taken in Mills River, N.C.

DESCRIPTION OF THE NEW VARIETY

Figure 1:
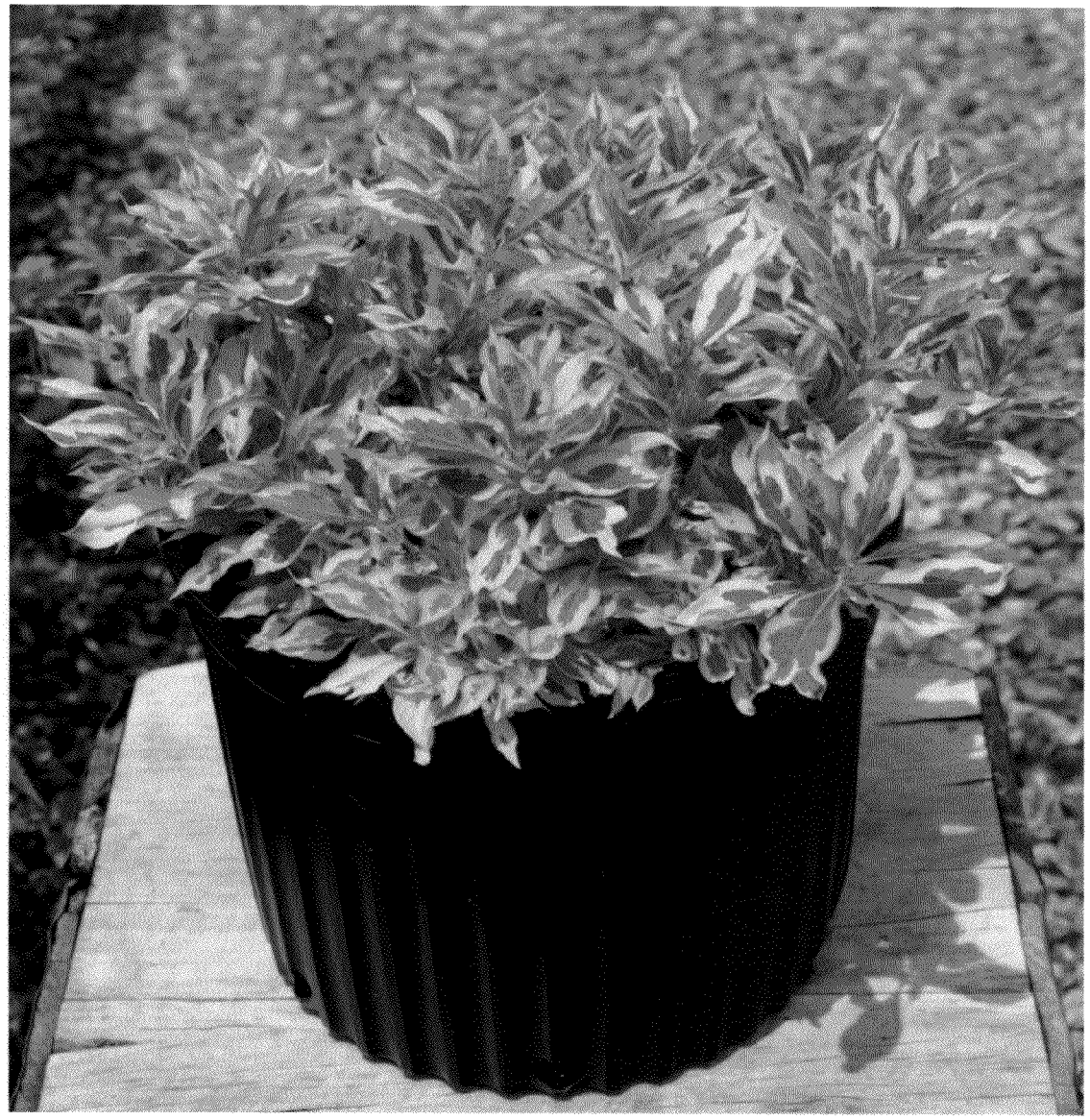
FIG. 1 shows a 1-year-old, container-grown, plant in August, 2004.
Figure 2:
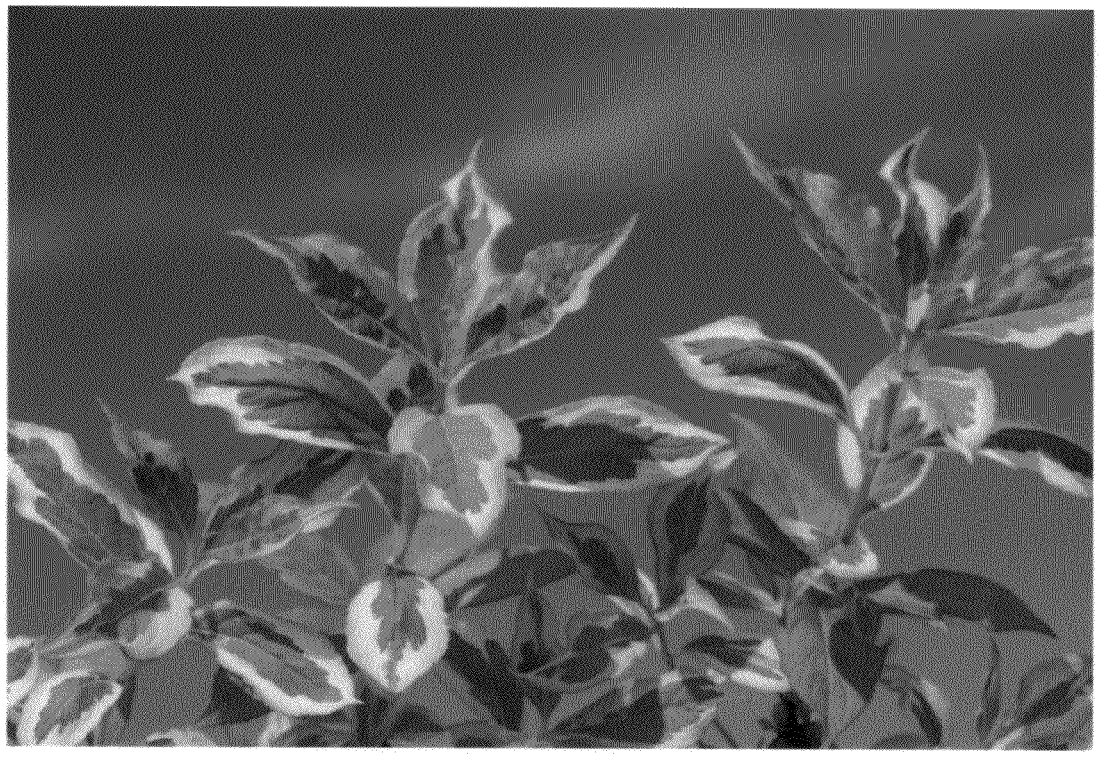
FIG. 2 shows the foliage in June, 2004 of a 1-year-old plant.
Figure 3:
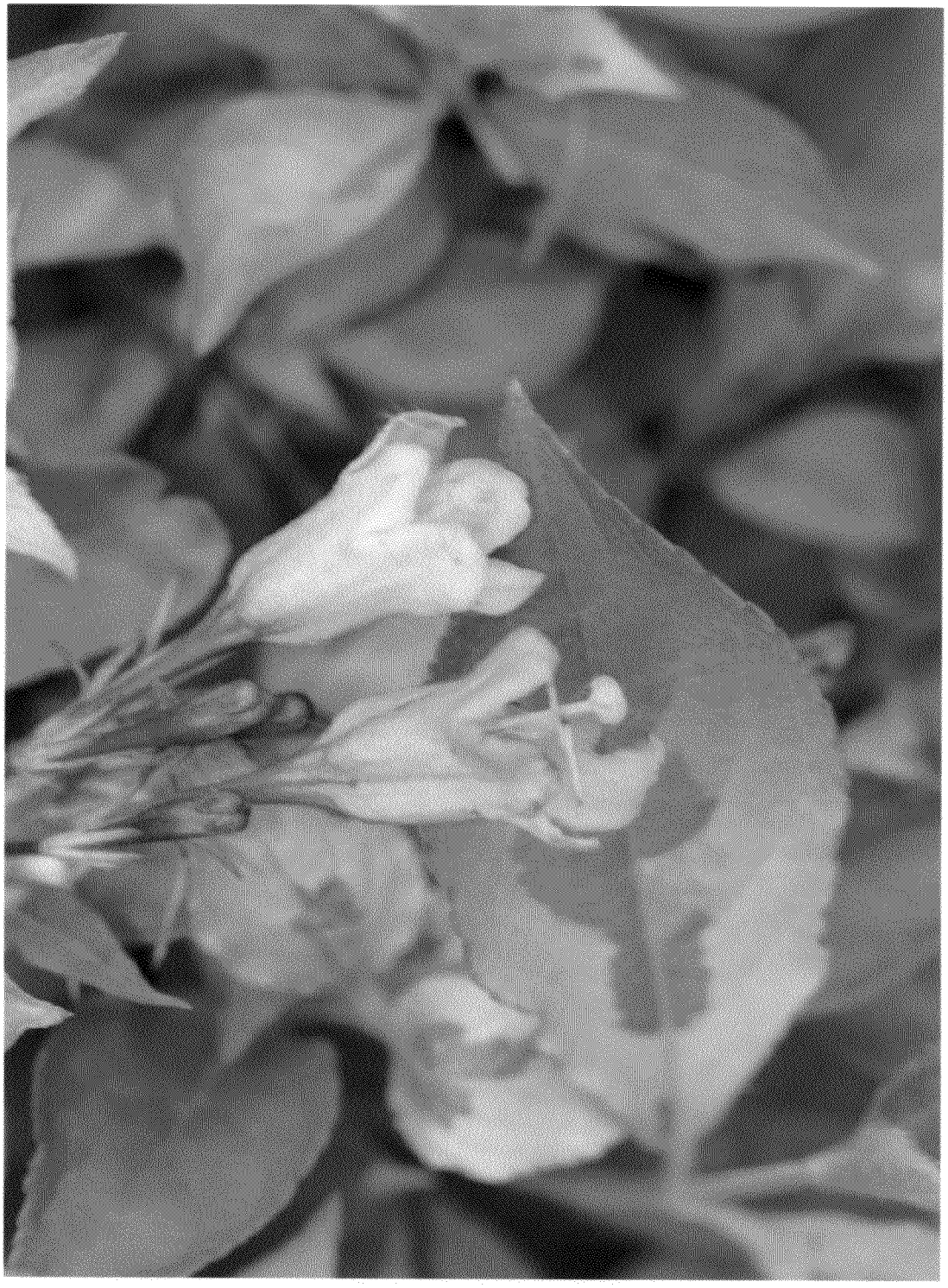
FIG. 3 shows the flowers in June, 2008 of a 5-year-old plant.

The following detailed description sets forth the distinctive characteristics of 'Sunset'. The detailed description was taken on 3-year-old container-grown plants in Mills River, N.C. in July 2010. Color references are to the R.H.S. Colour Chart of The Royal Horticultural Society of London (R.H.S.), 2001 Edition.

DETAILED BOTANICAL DESCRIPTION OF THE PLANT

Classification:
- *Botanical name.*—*Weigela florida.*
- *Common name.*—*Weigela.*
- *Denomination.*—'Sunset'.

Plant description:
- *Growth Habit.*—Compact, semi-dwarf habit.
- *Plant shape.*—Low, mounded.
- *Height at maturity.*—45.0 cm.
- *Width at maturity.*—65.0 cm.

Stem:
- *Mature stem color.*—RHS 177B.
- *Immature stem color.*—RHS 146C.
- *Mature stem texture.*—Strongly lenticellate to furrowed, cylindrical, tomentulose having lost the two clearly defined internodal alternate rows of hairs.
- *Immature stem texture.*—Lenticellate, slightly quadrangular having two opposite tomentose corners. The tomentose opposite corners alternate between nodes.

Leaves:

*Type.*—Deciduous.

*Arrangement.*—Alternate.

*Shape.*—Lanceolate to elliptic.

*Apex.*—Acuminate.

*Base.*—Cuneate to attenuate.

*Margin.*—Serrulate and undulate.

*Mature leaf size.*—Length: 10.0 cm. Width: 4.0 cm.

*Immature/developing leaf color.*—Adaxial (upper) surface: Variegated; central area is RHS 138A, variable from leaf to leaf including RHS 151A, RHS 151B, RHS 151C, RHS 152A, RHS 153A, RHS 144A, RHS 1C, RHS 1D, RHS 9C, occasionally with some diffuse RHS 143C, often flushed with RHS 180B. Abaxial (lower) surface: Variegated; central area RHS 146B, RHS,160A margin.

*Mature leaf color.*—Adaxial (upper) surface: Generally variegated with central area RHS 137C, margin including RHS 160A and RHS 137C; occasionally all green, RHS 137C; fall foliage color includes a combination of RHS 180A to RHS 180C and RHS 1D. Abaxial (lower) surface: Central area is RHS N138B, margin is RHS 143B; occasionally all green, RHS N138B.

*Mature/developed leaf texture.*—Adaxial (upper) surface: Glabrous. Abaxial (lower) surface: Glabrous, veins slightly pubescent.

*Leaf attachment.*—Petiolate.

*Petiole.*—Length: 1.0 cm. Width: 2.0 mm. Color: RHS 142B.

Flowers:

*Type.*—Single, funnelform-campanulate flowers arranged in terminal and axillary pairs or clusters of three to four flowers.

*Flowering season.*—Early spring through late spring; in May in Mills River, N.C.

*Lastingness of flowers on the plant.*—6 to 8 weeks.

*Fragrance.*—Absent.

*Length at anthesis.*—Average is 3.5 cm.

*Diameter at anthesis.*—2.5 cm.

*Abaxial color at anthesis.*—Proximal end RHS N66C changing to RHS 73A at distal end.

*Self-cleaning or persistent.*—Self-cleaning.

*Length of corolla tube*.—Average is 1.7 cm.

*Color of corolla tube*.—RHS N66 for both inner and outer surfaces.

*Lobes.*—Number of lobes per flower: 5. Shape: Obtuse. Abaxial Color: RHS 73A. Adaxial color: RHS 73A. Abaxial surface texture: Puberulous. Adaxial Surface texture: Glabrous. Length: 1.2 cm to 1.5 cm. Width: 1.0 cm to 1.3 cm.

*Sepals.*—Shape: Linear/lanceolate. Arrangement: Rotate. Length: 9.0 mm. Width: 1.0 mm. Color: RHS N155B with a blush of RHS 69C on both upper and lower surfaces. Surface texture: Glabrous.

*Calyx.*—Shape: Connate. Length: 11.0 mm. Diameter: 6.0 mm.

*Pedicels.*—Length: 10-15.0 mm. Diameter: 2.0 mm. Color: RHS 144C and tinged with RHS 53A. Texture: glabrous.

*Buds*. —Color: RHS 67C. Shape: claviform. Length: 12.0 to 15.0 mm. Proximal width: 1.0 mm to 1.5 mm. Distal width: 3.4 mm to 4.5 mm.

Reproductive organs:

*Stamen.*—Quantity per flower: 5. Anther: Shape: Ovoid. Color: RHS 155A. Pollen color: RHS 155A. Pollen amount: Moderate.

*Pistil.*—Quantity per flower: 1.

*Stigma.*—Shape: Globular. Color: RHS 155D.

*Style.*—Length: 3.8 cm. Color: RHS 155D.

Fruit: No fruit have been observed.

Seed: No seed have been observed.

Disease and insect resistance: No significant disease or insect pests have been observed.

COMPARISON WITH PARENTAL AND COMMERCIAL VARIETIES

'Sunset' is distinguished from the parental variety 'Alexandra' (U.S. Plant Pat. No. 10,772) in that 'Sunset' has lanceolate to elliptic-shaped leaves and shorter penduncles (1.5 cm), while 'Alexandra' has elliptic to ovate/oblong-shaped leaves and longer peduncles (2.0 cm to 2.5 cm).

'Sunset' is distinguished from other varieties by its semi-dwarf size and unique colors of the variegated foliage. Specifically, 'Sunset' has an intermediate mature size that is smaller than the commercial varieties 'Kolsunn' (U.S. Plant Pat. No. 13,567), 'Kolmagira' (U.S. Plant Pat. No. 20,384), and 'Kolmas' (U.S. Plant Pat. No. 16,452), yet larger than 'Verweig' (U.S. Plant Pat. No. 16,824). 'Sunset' also has unique colors expressed throughout the variegated foliage that include a combination of multicolored margins that range and include ivory yellow (RHS 160A), yellow (RHS 9C and RHS 1D), yellow-green (RHS 151C), green (RHS 143C), and red (RHS 180A to RHS 180C) depending on plant age and the time of year (see Table 1 for comparison with other cultivars).

TABLE 1

Comparison of 'Sunset' with other varieties of weigela

| Trait | Variety | | |
|---|---|---|---|
| | 'Sunset' | 'Verweig' | 'Kolsunn' |
| Plant height | 45.0 cm | 24.0 cm | 2.0 m |
| Plant width | 65.0 cm | 40.0 cm | 2.0 m |
| Center color of developing leaves | RHS 138A | RHS 141A | RHS 146A to RHS 137A |
| Margin color of developing leaves | RHS 151C to RHS 9C, RHS 143C RHS 180B | RHS 158A and RHS 183A | RHS 158A and RHS 58A |
| Center color of mature leaves | RHS 137C | RHS 141A | RHS 147A and RHS 137A |
| Margin color of mature leaves | RHS 160A and RHS 137C | RHS 158A, RHS 183A | RHS 158C to RHS158D |

| Trait | Variety | |
|---|---|---|
| | 'Kolmagira' | 'Kolmas' |
| Plant height | 86.0 cm | 1.25 m |
| Plant width | 93.0 cm | 1.5 m |
| Center color of developing leaves | RHS 139A | RHS 137A |

TABLE 1-continued

| Comparison of 'Sunset' with other varieties of weigela | | |
|---|---|---|
| Margin color of developing leaves | RHS 153C to RHS 153D and RHS 185A | RHS 1D, RHS 180A |
| Center color of mature leaves | RHS 139A | RHS 147A |
| Margin color of mature leaves | RHS 151C and RHS 151D, RHS 163A and RHS N163D | RHS 155A and RHS 157A, RHS 180A |

I claim:

1. A new and distinct variety of *weigela* shrub as described and shown herein.

* * * * *